US010104925B2

(12) United States Patent
Farmer et al.

(10) Patent No.: US 10,104,925 B2
(45) Date of Patent: Oct. 23, 2018

(54) GARMENT WITH ALTERED STRESS PROFILE

(71) Applicant: INVISTA NORTH AMERICA S.A R.L., Wilmington, DE (US)

(72) Inventors: Douglas K. Farmer, Greensboro, NC (US); Carmen A. Covelli, Chadds Ford, PA (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 67 days.

(21) Appl. No.: 15/161,749

(22) Filed: May 23, 2016

(65) Prior Publication Data

US 2016/0286879 A1 Oct. 6, 2016

Related U.S. Application Data

(62) Division of application No. 12/354,030, filed on Jan. 15, 2009, now abandoned.

(Continued)

(51) Int. Cl.
*A41C 3/00* (2006.01)
*A41D 31/00* (2006.01)
(Continued)

(52) U.S. Cl.
CPC ............ *A41D 31/00* (2013.01); *A41B 1/08* (2013.01); *A41B 9/001* (2013.01); *A41B 9/04* (2013.01); *A41B 9/06* (2013.01); *A41B 11/003* (2013.01); *A41B 11/14* (2013.01); *A41B 17/00* (2013.01); *A41C 1/00* (2013.01); *A41C 3/00* (2013.01); *A41C 3/10* (2013.01); *A41D 1/00* (2013.01); *A41D 1/04* (2013.01); *A41D 1/06* (2013.01); *A41D 1/14* (2013.01); *A41D 1/18* (2013.01); *A41D 1/22* (2013.01); *A41D 3/02* (2013.01); *A41D 3/04* (2013.01); *A41D 3/08* (2013.01); *A41D 7/00* (2013.01); *A41D 10/00* (2013.01); *A41D 13/0002* (2013.01); *A41D 13/002* (2013.01); *A41D 13/012* (2013.01); *A41D 13/04* (2013.01); *A41D 13/1209* (2013.01);
(Continued)

(58) Field of Classification Search
CPC ........... A41C 3/0014; A41C 3/00; B32B 5/02; B32B 5/18; B32B 26/06; B32B 7/10; C08G 18/0823; C08G 18/0852
USPC ......................................... 450/39, 54–57, 38
See application file for complete search history.

(56) References Cited

U.S. PATENT DOCUMENTS 4,701,964 A  10/1987  Prunesti et al.
4,826,894 A   5/1989  Markusch et al.
(Continued)

FOREIGN PATENT DOCUMENTS

JP        17-290613        10/2005

OTHER PUBLICATIONS

Siggia, S., "Quantitative Organic. Analysis via Functional Group", 3rd Edition, Wiley & Sons, New York, 1963, pp. 559-561.
(Continued)

*Primary Examiner* — Gloria Hale
(74) *Attorney, Agent, or Firm* — Bridget C. Sciamanna; Kathleen A. Tyrell

(57) ABSTRACT

Included are articles such as garments including polymer film compositions to alter the stress profile of the garment which is exhibited during wear of the garment. The polymer film may be bonded to the fabric to provide a fabric/film laminate.

9 Claims, 10 Drawing Sheets

Related U.S. Application Data

(60) Provisional application No. 61/021,241, filed on Jan. 15, 2008.

(51) Int. Cl.

| | | |
|---|---|---|
| *A41B 17/00* | (2006.01) | |
| *A41C 3/10* | (2006.01) | |
| *A41B 1/08* | (2006.01) | |
| *A41B 9/00* | (2006.01) | |
| *A41B 9/04* | (2006.01) | |
| *A41B 9/06* | (2006.01) | |
| *A41B 11/00* | (2006.01) | |
| *A41B 11/14* | (2006.01) | |
| *A41C 1/00* | (2006.01) | |
| *A41D 1/00* | (2018.01) | |
| *A41D 1/04* | (2006.01) | |
| *A41D 1/06* | (2006.01) | |
| *A41D 1/14* | (2006.01) | |
| *A41D 1/18* | (2006.01) | |
| *A41D 1/22* | (2018.01) | |
| *A41D 3/02* | (2006.01) | |
| *A41D 3/04* | (2006.01) | |
| *A41D 3/08* | (2006.01) | |
| *A41D 7/00* | (2006.01) | |
| *A41D 10/00* | (2006.01) | |
| *A41D 13/00* | (2006.01) | |
| *A41D 13/002* | (2006.01) | |
| *A41D 13/012* | (2006.01) | |
| *A41D 13/04* | (2006.01) | |
| *A41D 13/12* | (2006.01) | |
| *A41D 17/00* | (2006.01) | |
| *A41D 20/00* | (2006.01) | |
| *A41D 25/00* | (2006.01) | |
| *A41D 27/02* | (2006.01) | |
| *A41D 29/00* | (2006.01) | |
| *A41F 9/00* | (2006.01) | |
| *A42B 1/00* | (2006.01) | |
| *A42B 5/00* | (2006.01) | |
| *A61F 5/37* | (2006.01) | |
| *A61F 13/00* | (2006.01) | |
| *B32B 5/02* | (2006.01) | |
| *B32B 5/18* | (2006.01) | |
| *B32B 27/06* | (2006.01) | |

(52) U.S. Cl.
CPC ............ *A41D 17/00* (2013.01); *A41D 20/00* (2013.01); *A41D 25/00* (2013.01); *A41D 27/02* (2013.01); *A41D 29/00* (2013.01); *A41F 9/00* (2013.01); *A42B 1/00* (2013.01); *A42B 5/00* (2013.01); *A61F 5/3715* (2013.01); *A61F 13/00038* (2013.01); *B32B 5/02* (2013.01); *B32B 5/18* (2013.01); *B32B 27/06* (2013.01); *A41B 2400/38* (2013.01); *A41B 2500/50* (2013.01); *A41C 3/0014* (2013.01); *B32B 2437/00* (2013.01)

(56) References Cited

U.S. PATENT DOCUMENTS

| | | |
|---|---|---|
| 5,162,481 A | 11/1992 | Reid et al. |
| 5,391,343 A | 2/1995 | Dreibelbis et al. |
| 5,447,462 A | 9/1995 | Smith et al. |
| 5,461,122 A | 10/1995 | Yilgor et al. |
| 5,660,577 A | 8/1997 | Modena |
| 5,879,596 A | 3/1999 | Roach |
| 5,916,829 A | 6/1999 | Girard et al. |
| 6,000,994 A | 12/1999 | Salotto |
| 6,203,901 B1 * | 3/2001 | Kosinski ............... C08G 18/10 428/364 |
| 6,238,266 B1 | 5/2001 | Vogt |
| 6,287,168 B1 | 9/2001 | Rabinowicz |
| 6,645,040 B2 | 11/2003 | Rabinowicz et al. |
| 6,837,771 B2 | 1/2005 | Falla |
| 6,966,815 B2 | 11/2005 | Weinerth |
| 7,192,332 B2 * | 3/2007 | Liu ...................... A41C 3/0014 450/39 |
| 7,240,371 B2 | 7/2007 | Liu et al. |
| 7,300,331 B2 | 11/2007 | Baran et al. |
| 7,425,516 B2 * | 9/2008 | Kocher ............. C08G 18/0852 428/151 |
| 7,563,152 B2 | 7/2009 | Liu |
| 7,682,219 B2 | 3/2010 | Falla |
| 7,749,207 B2 | 7/2010 | Rossi et al. |
| 8,058,343 B2 | 11/2011 | Liu et al. |
| 2006/0183849 A1 * | 8/2006 | Liu .................... C08G 18/0823 524/589 |
| 2006/0183851 A1 * | 8/2006 | Liu ...................... A41C 3/0014 524/589 |
| 2006/0183852 A1 * | 8/2006 | Liu ........................ B32B 7/12 524/591 |
| 2007/0082579 A1 | 4/2007 | Baran et al. |
| 2007/0213457 A1 | 9/2007 | Liu et al. |
| 2008/0004395 A1 * | 1/2008 | Covelli ............. C08G 18/0823 524/591 |
| 2008/0153388 A1 * | 6/2008 | Liu ........................ A41C 3/00 450/39 |
| 2009/0181599 A1 | 7/2009 | Farmer et al. |
| 2009/0264462 A1 * | 10/2009 | Carroll ................ A61K 31/451 514/307 |

OTHER PUBLICATIONS

Walter et al., "Solving Common Coating Flaws in Reverse Roll Coating", Converting Magazine, National Starch & Chemical Company, Delivered at AIMCAL, Oct. 2003, 4 pages.

* cited by examiner

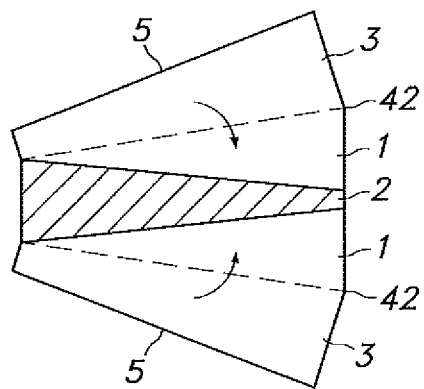
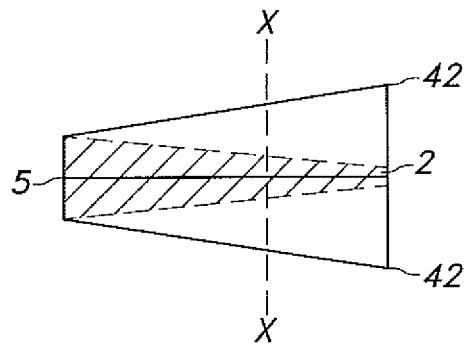
FIG. 14          FIG. 14A
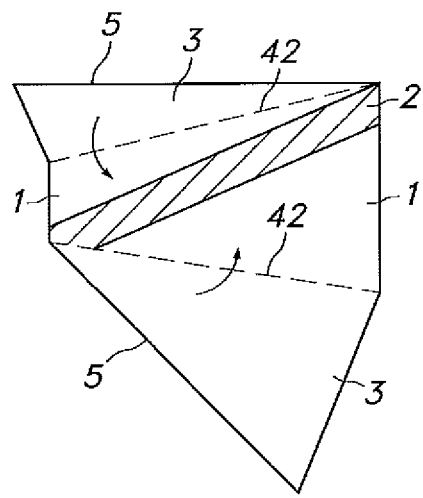
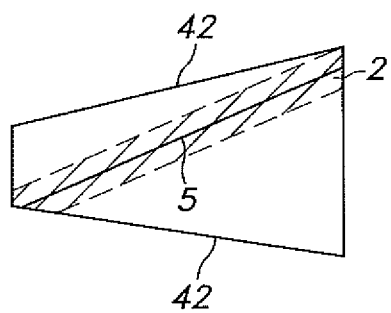
FIG. 15          FIG. 15A
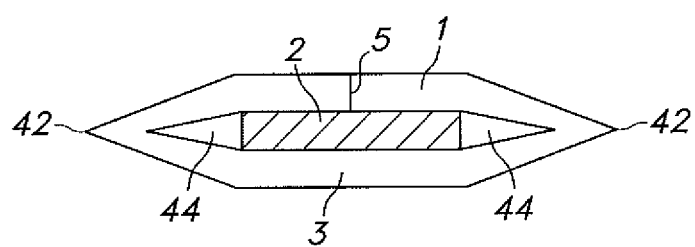
FIG. 16

GARMENT WITH ALTERED STRESS PROFILE

CROSS-REFERENCE TO RELATED APPLICATIONS

This application is a divisional of U.S. application Ser. No. 12/354,030, filed on Jan. 15, 2009, now abandoned, which claims priority to U.S. Provisional Patent Application No. 61/021,941, filed Jan. 15, 2008, the entire contents of all of which are incorporated by reference herein.

BACKGROUND OF THE INVENTION

Field of the Invention

The present invention relates to articles such as garments including body shaping garments and performance enhancing garments that include an altered stress profile. The article or garment includes one or more layers of material such as fabric and/or polyurethane foam in combination with a polyurethaneurea composition.

Summary of Related Technology

Garments provide a variety of different functions including, but not limited to, warmth, fashion, and comfort. Two goals of body shaping garments include support and comfort either of which can be compromised due to the other. One reason for reduction in comfort is that garments designed for body-shaping or support frequently have areas where increased pressure is exerted on the wearer of the garment. For example, if one imagines a band of material wrapped around a person where the band has a wide section and a narrow section, the force within the band length of the band is the same, however, this force is distributed more evenly across the wide portion of the band compared to thin portion. The result is an increased pressure at the point where the narrow portion is in contact with the body.

The areas of increased pressure can result in discomfort to the wearer. Therefore, there is a need for garments that overcome these deficiencies by redistributing the pressure by altering the stress profile of the garment, including providing additional support where desired, and providing greater comfort to the wearer.

Another issue experience by body-shaping garments, such as laminated foam garments, is fabric growth. This is particularly an issue with one-piece laminated foam brassieres. There is a need to provide a method of redistributing or controlling stress within the garment to prevent fabric growth.

SUMMARY OF THE INVENTION

In some embodiments are an article including a garment including:
(a) one or more sections of fabric;
wherein each section of fabric has a stress profile; and
(b) one or more polymeric films attached to one or more sections of fabric to form a fabric laminate;
wherein the fabric laminate has an altered stress profile. These garments can be designed to prevent greater comfort to the wearer in addition to reducing fabric growth.

A garment including a brassiere having a wing portion, the wing portion including a polymeric film in the shape or form of a narrow strip, a triangular shape, or the shape of the wing portion geometrically inverted to the wing portion.

A brassiere which includes an assembly of layers of material defining a pair of breast cups with a bridge between said cups, said assembly comprising at least a first and a second layer of material molded to define the shape of the breast cups, each of said breast cups including a lower periphery which extends from said bridge and toward a side periphery that extends from said lower periphery to a top portion of each of said breast cups where a strap is optionally attached;
wherein adjacent to either or both each of said lower and side peripheries of said breast cups, there is embedded in or adhered to said layers of material of said assembly a polymeric film including a polyurethaneurea cast and dried from a polyurethaneurea dispersion.

Methods of preparing garments including an altered stress profile are also included.

BRIEF DESCRIPTION OF THE DRAWINGS

FIG. 14 shows a portion of fabric including a polymer film region.
FIG. 14A shows a multiple layer portion of fabric including a polymer film region.
FIG. 15 shows a portion of fabric including a polymer film region.
FIG. 15A shows a multiple layer portion of fabric including a polymer film region.
FIG. 16 shows a cross-section of the multiple layer fabric of FIG. 14A along line X-X.

DETAILED DESCRIPTION OF THE INVENTION

Figure 1:
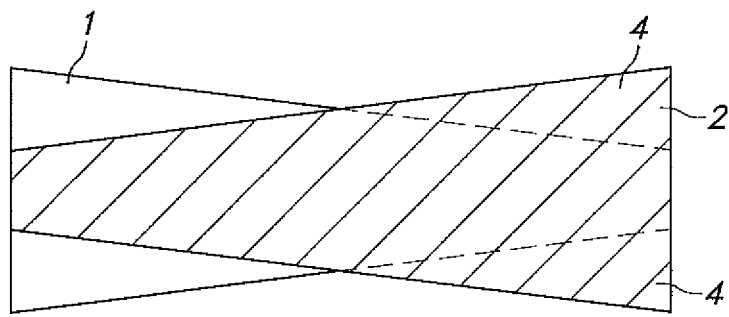
FIG. 1 shows a portion of fabric including a geometrically inverted polymer film.

For the purposes of this invention, the term "stress profile" of a fabric is defined as a physical pressure, pull, or other force that is exerted on a fabric accounting for various different forces that can be measured at various points throughout the garment. The stress profile can be observed in any fabric such as a fabric used in a garment. One example of a stress profile of a fabric is noted for body shaping garments where the stress or pressure exerted on the garment will vary as the garment is being worn due to wearer movement. Another example is for a support garment such as a brassiere where the stress on the bottom of the cup portions may be greater than that on the top of the cup portions.

For the purposes of this invention, the term "geometrically inverted" is meant to include embodiments where a film of the same geometric shape as the fabric with which it will be laminated has been rotated with respect to the fabric. The film may be larger, smaller, or the same size as the fabric section. This also includes, but is not limited to, where film and fabric of size and dimension are designed inversely proportionate to the modulus of the film and fabric, respectively.

As used herein, the term "non-linear" includes shapes other than a straight line. This includes, but is not limited to, curved shapes, arc shapes, and wavy shapes.

As used herein, the term "narrow strip" refers to a shape having a length and a width where the length is at least twice the width. The length may vary and depends on the size of the garment to which it is applied.

As used herein, the term "porous" refers to a substrate that includes voids or holes in the surface or at any point within or through the thickness of the substrate or to any material of which the articles of the present invention may come into contact.

As used herein, the term "pressing" or "pressed" refers to an article that has been subjected to heat and/or pressure to provide a substantially planar structure.

As used herein, the term "foam" refers to any suitable foam that may be used in fabric construction such as polyurethane foam.

As used herein, the term "dispersion" refers to a system in which the disperse phase consists of finely divided particles, and the continuous phase can be a liquid, solid or gas.

As used herein, the term "aqueous polyurethane dispersion" refers to a composition containing at least a polyurethane or polyurethane urea polymer or prepolymer (such as the polyurethane prepolymer described herein), optionally including a solvent, that has been dispersed in an aqueous medium, such as water, including de-ionized water.

As used herein, the term "solvent," unless otherwise indicated, refers to a non-aqueous medium, wherein the non-aqueous medium includes organic solvents, including volatile organic solvents (such as acetone) and somewhat less volatile organic solvents (such as MEK, or NMP).

As used herein, the term "solvent-free" or "solvent-free system" refers to a composition or dispersion wherein the bulk of the composition or dispersed components has not been dissolved or dispersed in a solvent.

As used herein, the term "article" refers to an article which comprises a dispersion or shaped article and a substrate, for example a textile fabric, which may or may not have at least one elastic property, in part, due to the application of a dispersion or shaped article as described herein. The article may be in any suitable configuration such as one-dimensional, two-dimensional and/or three-dimensional.

As used herein, the term "fabric" refers to a knitted, woven or nonwoven material. The knitted fabric may be flat knit, circular knit, warp knit, narrow elastic, and lace. The woven fabric may be of any construction, for example sateen, twill, plain weave, oxford weave, basket weave, and narrow elastic. The nonwoven material may be meltblown, spun bonded, wet-laid, carded fiber-based staple webs, and the like.

As used herein, the term "hard yarn" refers to a yarn which is substantially non-elastic.

As used herein, the term "molded" article refers to a result by which the shape of an article or shaped article is changed in response to application of heat and/or pressure.

As used herein, the term "derived from" refers to forming a substance out of another object. For example, a film may be derived from a dispersion which can be dried.

As used herein, the term "modulus" refers to a ratio of the stress on an item expressed in force per unit linear density or area.

As used herein, the term "fabric growth" is meant to include the natural tendency of fabrics to stretch over time or during wear that is not recovered (i.e., not elastic).

For the purposes of this invention, the terms "polymer film," "polymer solution," and "polymer dispersion" are used interchangeably to describe a substantially two-dimensional or relatively flat layer of polymer, optionally in water or solvent, that may or may not require application to a substrate for support.

As used herein, the term "fabric laminate" refers to a multiple layer article including at least one fabric layer and at least one polymer layer that have been attached or bonded together. The methods of attachment include, but are not limited to, gluing, heating, application of pressure, and combinations thereof.

As used herein, the term "performance-enhancing" in reference to a garment refers to a garment that reduces fatigue or maintains performance-ability of the wearer of the garment. For example, an athlete may wear a performance-enhancing garment during competition to reduce fatigue and/or maintain competitive performance.

In some embodiments are garments including a polymer film that alters the stress profile of the garment. This includes equally distributing stress throughout the garment as well as providing a "stress gradient" where additional support is desired. The stress gradient provides areas of preselected stress to redistribute the stress such as from an area of lower stress to an area of greater stress within the fabric of the garment. One example of a stress gradient is useful for a brassiere. The polymer film may be included in a bra cup to provide a stress gradient that provides greater stress for support at the bottom of the cup and lower stress at the top of the cup.

The articles of some embodiments include at least one layer of a polymer film such as a polyurethaneurea composition in the form of a film or dispersion. These articles have at least two layers including the polymer film. The polymer film may be placed adjacent to or between the layers of material such as fabric or foam and also may provide stretch and recovery, increased elastic modulus, adhesion, moldability, shape retention, and flexibility properties for the article. These articles may be formed into fabrics and/or garments.

A variety of polymers are useful with the articles of some embodiments and more than one layer of film may be included. These include polymer films of polyurethane, polyurethaneurea, polyolefin, and combinations thereof. Examples of useful polyolefin resins are commercially available under the brand name VISTAMAXX by ExxonMobil, such as VISTAMAXX® 1100 and VISTAMAXX® 2100 which may be melted and shaped into a film or prepared as a nonwoven.

A variety of different polyurethaneurea compositions are useful with the films and dispersions of some embodiments. For example, the films of the some embodiments may be cast from a solution, an aqueous dispersion, or a substantially solvent free aqueous dispersion. Many such solutions or dispersions are known in the art. For example, a polyurethaneurea solution such as a spinning solution from a commercial spandex production line may be used to cast a film, according to some embodiments of the present invention. Specific examples of aqueous dispersions and films cast from them which are useful with the present invention are described hereinbelow.

In an embodiment where the article includes a multiple layer article including three or more layers where one layer is a film, the film may be an intermediate layer between two fabric layers, between two foam layers, between a fabric layer and a foam layer, or adjacent to a foam layer which is adjacent to a fabric layer. Combinations of these fabric/foam/film arrangements are also contemplated. For example, the article may include, in order, a fabric layer, a foam layer, a film layer, a foam layer, and a fabric layer. This article includes two separate fabric layers, two separate foam layers and a film layer. In any of these embodiments, the polymer film may be replaced with a polymer solution or dispersion. Therefore, the article may include one or more polymer film and one or more polymer dispersion layers.

In another embodiment, a single layer of a fabric or foam may be folded to form two or more layers of the multiple layer article with a polymer film, solution, or dispersion as an intermediate layer (where the film may be considered 'embedded' within the article). In this embodiment, the article may then also be molded or pressed to a desired shape, such as for a body shaping garment. Where a polymer film is placed at the point of folding, the tape may provide additional stretch recovery power, such as at a hem or for a body shaping garment, to provide additional support. This is also useful in a garment such as an underbust bra where the film/tape placement may provide increased wall strength or rigidity and may keep the garment from rolling at the edge. The polymer film may also be placed at the point where the edges of the single layer meet which form the double layer fabric as shown in FIG. 16 which is described hereinbelow in more detail. Additional fabric or foam layers may also be included within the folded over layer as desired. For example, a fabric layer may be folded over to form two layers where a polymer film and a foam are included within the folded area.

In an embodiment that includes two or more layers, the polyurethaneurea composition may form an external layer. Including the polyurethaneurea composition on an external surface forms many advantageous functions. For example, the polyurethaneurea composition may provide an anchor or area of increased friction to reduce the relative movement between the article including the polyurethaneurea composition and an external substrate. This is particularly useful when the article is an undergarment including a skin-contacting surface (where the wearer's skin is the substrate). Alternatively, the substrate may be outer clothing which is in contact with the polyurethaneurea composition of the inventive article. Where the substrate is outer clothing of a wearer and the article is worn as an undergarment, the article prevents or reduces the relative movement of the outer garment. In addition, an outer garment (e.g. a dress) may include a polyurethaneurea composition to maintain the relative placement of an inner garment (e.g. a slip).

After the layers of fabric, foam, and the film have been selected, they may subsequently be adhered through pressing or molding to form flat or shaped articles (including articles having three-dimensions such as a molded brassiere cup). The processes to prepare the pressed and molded articles of some embodiments include the use of pressure and heat as necessary. For example, heat may be applied at about 150° C. to about 200° C. or about 180° C. to about 190° C., including about 185° C. for a sufficient time to achieve a molded article. Suitable times for application of heat include, but are not limited to, from about 30 sec to about 360 sec including from about 45 sec to about 120 sec. Bonding may be effected by any known method, including but not limited to, microwave, infrared, conduction, ultrasonic, pressure application over time (i.e. clamping) and combinations thereof.

Due the application of heat and pressure to the articles including polyurethaneurea films or dispersion and given that films and fabrics are themselves porous materials, it is recognized that the film or dispersion may partially or completely impregnate the fabric or foam of the article. For example, the polyurethaneurea composition may form a layer which is partially separate from the surrounding layers, or may be completely transferred to the surrounding layer or layers to form an integrated article without a distinguishably separate polyurethaneurea composition layer.

One application of the multi-layer articles of the present invention is body-shaping garments such as brassieres (especially in cups or wings) other women's undergarments and men's undergarments. These articles can provide the desirable features of body shaping and support while still providing comfort, breathability, air permeability, moisture/vapor transport, wicking, and combinations thereof. In the articles of some embodiments of the present invention, the layers may take on predetermined shapes and may be arranged in predetermined orientations relative to each other in the design of a molded or shaped article such as the cups of a brassiere construction. The layers of these fabrics may be used either alone or in combination with other materials that are sewn, glued or otherwise applied to the fabrics.

In some embodiments there is a system for the construction of a garment with integrated shaping ability provided by the fabric. This system of construction may be used in a variety of different garment constructions such as activewear, sportswear, men's and women's intimate apparel such as bras, underwear, panties, shaping garments, legwear and hosiery such as pantyhose, ready-to-wear garments such as denim jeans, camisoles, tailored shirts, and pants among others. This construction may be applied to any formable body area. While many advantages of the fabric constructions are included, it is further recognized that the utility is not limited to garments, but also finds applicability with any shapeable or formable medium, including cushions for furniture which are also subject to movement and potential slipping of a fabric in contact with the shapeable area.

In order to add additional support and other features, the polymer film composition may be added to different areas of the article. For example, it may either extend through the entire area of the article or to a selected portion to provide different benefits. For example, a brassiere may include a layered fabric of some embodiments in the cup portion. In the brassiere cup, it can be useful to use a portion of film in the lower portion of the cup for support, in a central portion of the cup for modesty, in the side portion for shaping, or in specific areas for embellishment or decoration.

In each of the figures, the polymer films are shown as a separate layer for clarity only. The polymer film on attachment may partially or completely fill the pores of the fabric or foam substrate.

In FIGS. 1-3, 8-9, and 14-15, a portion of fabric is shown having a substantially trapezoidal shape. Such a shape is useful as a bra wing portion, as discussed. However, although referred to a bra wing portion, the fabric portion may be useful in other areas of a garment and is shown to demonstrate an example of how a polymer film may be oriented with respect to the shape of the fabric to alter the stress-profile of the fabric. A variety of geometric shapes for both the fabric portion and the polymer film portion are contemplated and can be chosen based on the desired alteration of stress-profile. The alteration may be to provide comfort by distributing stress throughout the garment or to increase stress in portions of the garment to provide additional control or support.

As shown in FIG. 1, a polymer film composition 2 may be geometrically inverted onto a portion of a garment such as a bra wing portion 1, which is a substantially trapezoid shape, and is shown as a trapezoid. The corners 4 that overlap extend beyond the edges of the wing portion may be folded over or cut to shape of the polymer film.

Figure 2:
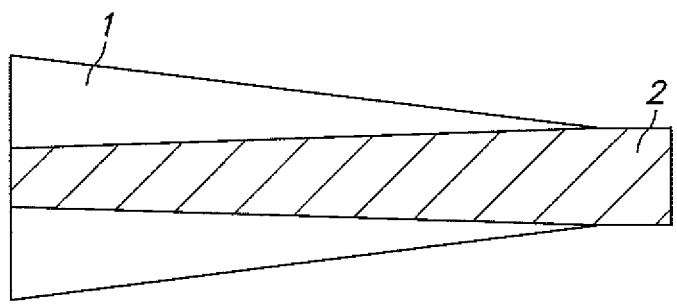
FIG. 2 shows a portion of fabric including a geometrically inverted polymer film.

As an alternative, FIG. 2 also shows a polymer film composition 2 that has been geometrically inverted onto a wing portion 1, however, while the film has substantially the same shape as the wing portion, it is reduced in size to avoid the overlapping corners 4 of FIG. 1, while still providing a altered stress profile.

In either FIG. 1 or FIG. 2, the fabric section 1 may be a wing including a trapezoid having a wide end and a shorter end. The polymeric film 2 also has a wide and a shorter end. The shorter end of the polymeric film is placed corresponding to the wide end of the fabric section and the wide end of the polymeric film is placed corresponding to the shorter end of the fabric section.

Figure 8:
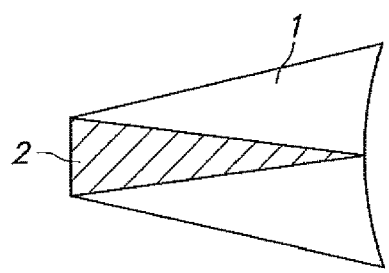
FIG. 8 shows a portion of fabric including a triangular shaped polymer film region.
Figure 9:
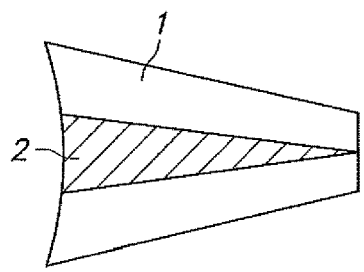
FIG. 9 shows a portion of fabric including a triangular shaped polymer film region.

FIG. 8 and FIG. 9 also show fabric portions 1 having a polymer film region 2 bonded to the fabric portion 1. In each of FIG. 8 and FIG. 9, the polymer film region has a triangular shape.

Figure 3:
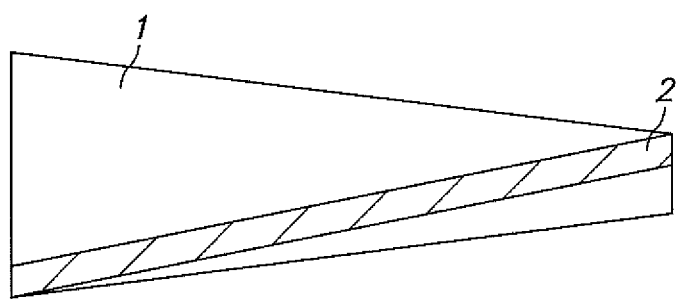
FIG. 3 shows a portion of fabric including a narrow strip of polymer film.

As shown in FIG. 3, another method of altering the stress profile of a garment, such as a wing 1 is to include a narrow strip of a polymer film 2. Although this polymer film shown appears substantially linear, it is understood that this may be modified to a non-linear shape depending on the manner of altering the stress profile that is selected. The film 2 may extend to the edges of the wing 1 as shown or may alternatively begin and end at intermediate portions of the wing 1. The film 2, may be oriented along a diagonal (as it appears in FIG. 3) or may be perpendicular to the wing edge.

In other words, the fabric section may have a top portion an intermediate portion and a bottom portion where the polymeric film is oriented adjacent to two or more portions of the fabric section. The polymer film may be oriented along a diagonal from the top of the fabric section to the bottom of the fabric section, along a diagonal at other portions within the fabric or perpendicular to the fabric section.

Figure 4:
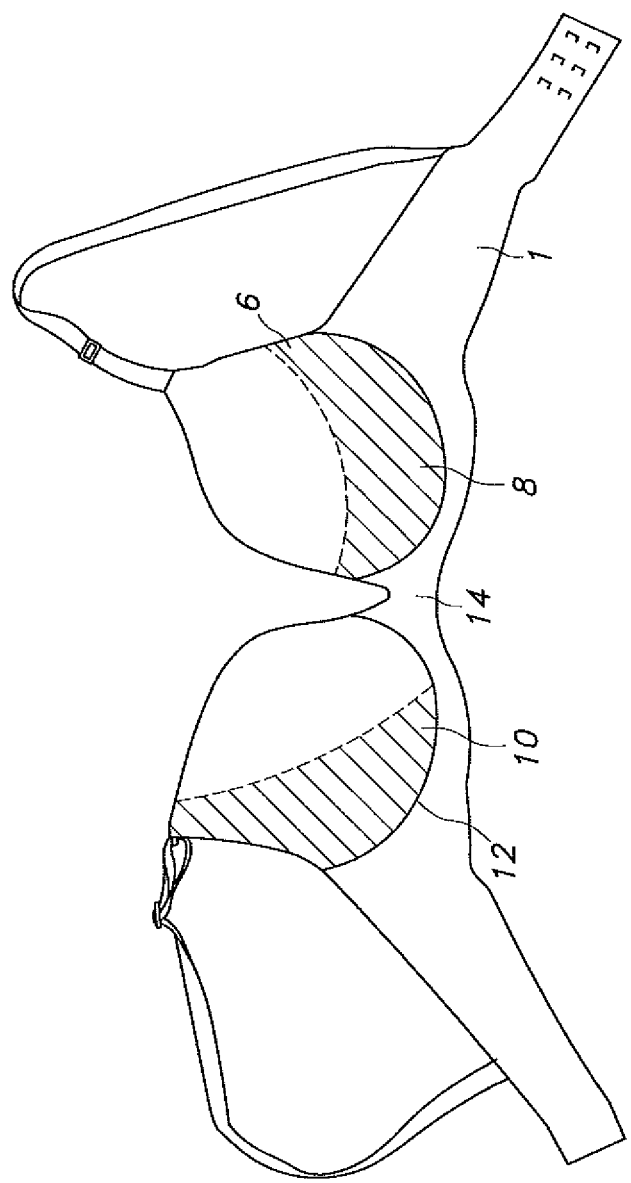
FIG. 4 shows a brassiere including polymer film regions along a lower and side periphery.

FIG. 4 shows a brassiere as an example of a garment that can include the polymer film to alter the garment's stress profile. The brassiere includes a wing portion 1 and two cup portions 6 and 10. The cup portion 6 includes a polymer film 8 located along the bottom periphery of the cup 6. The other cup includes a polymer film that is located along the side periphery 12. The side periphery film 12 and the bottom periphery film 8 can be used together or separately to adjust the stress profile of the garment to provide shaping and support. Although a brassiere is shown as the example, it is understood that this could apply to other formable areas of the body, such as the derriere.

Figure 5:
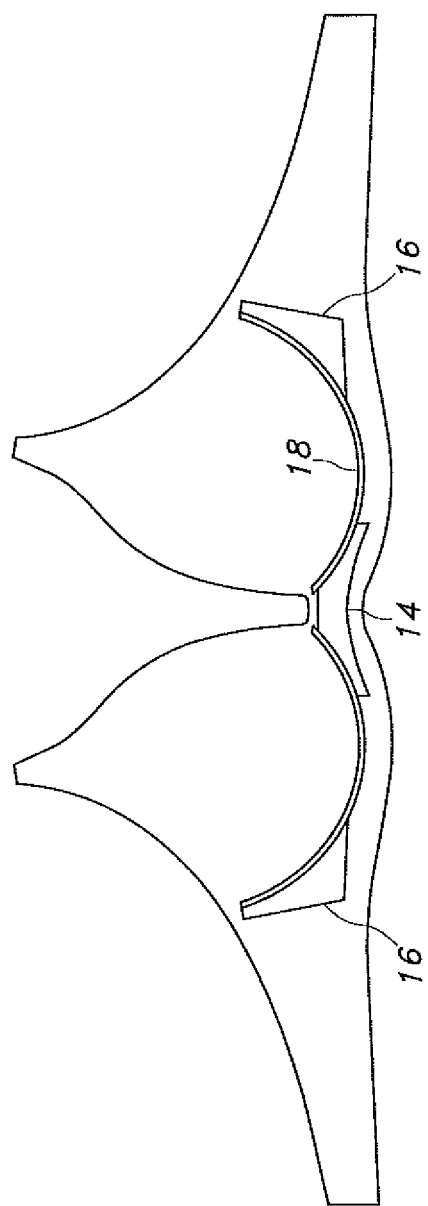
FIG. 5 shows a brassiere including polymer film regions.

FIG. 5 also shows a brassiere including an underwire portion 18. The underwire portion is also a potential cause of a pressure point in a brassiere. The addition of polymer films 14 and 16 can provide one or both of additional comfort and support by altering the stress profile to which the underwire portion 18 contributes.

Although the brassieres of FIGS. 4-7 appear to be back closure brassieres that include straps, it is understood that straps are optional and that a front closure (not shown) may be included in the area between the cups at 14.

Figure 6:
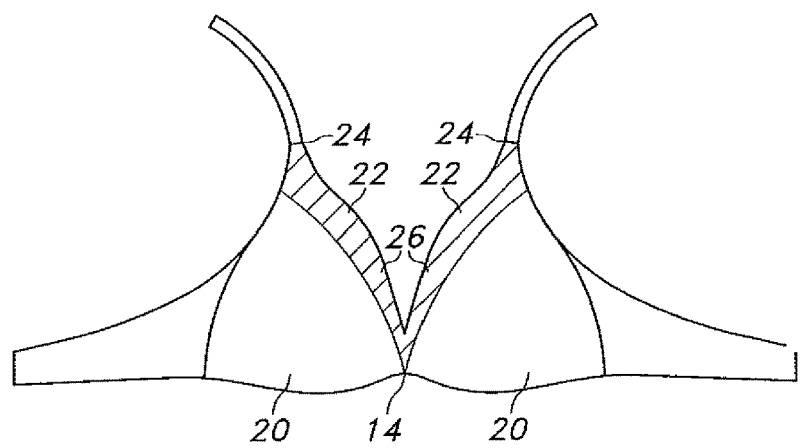
FIG. 6 shows a brassiere including polymer film regions.
Figure 7:
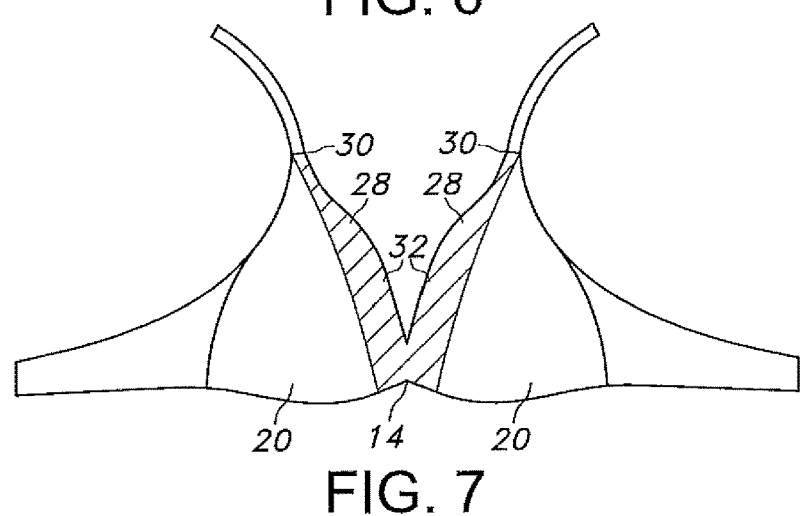
FIG. 7 shows a brassiere including polymer film regions.

The brassiere of FIG. 6 includes two cup portions 20 each having a polymer film portion 22 at the inner part of the cup. The stress profile of the cup portions 20 are altered by including the film portions 22 which may vary in width from the top part of the cup 24 which is wider as shown as the film portion 22 extends to the inner part of the cup 26. The opposite configuration is shown in FIG. 7, where the cup portions 20 include film portions 28 that vary in width from a narrow part at the top of the cup 30 extending to the bottom inner part of the cup 32. Altering the stress profile of this area of the brassiere can avoid pinch points while provide support or enhancement as desired. In order to achieve the desired effect, other geometries or configurations of the film portions 22 and 28 are contemplated.

Figure 10:
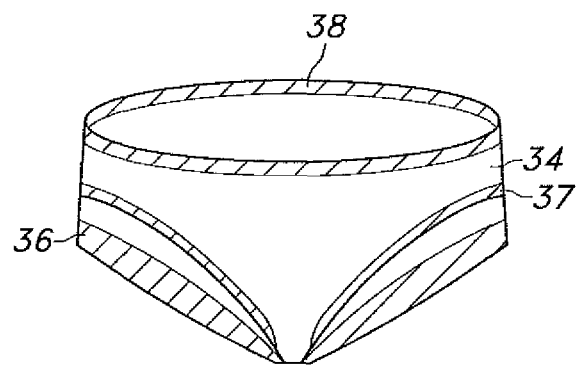
FIG. 10 shows a panty including polymer film regions.
Figure 11:
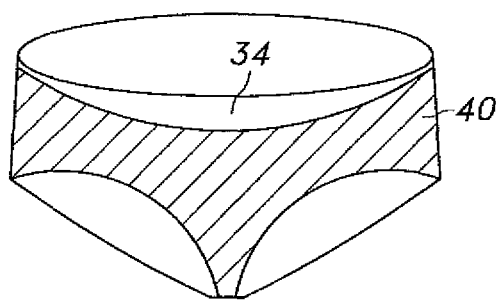
FIG. 11 shows a panty including polymer film regions.

FIG. 10 and FIG. 11 each show a panty 34 including different film portions 36, 37, 38 and 40. The film region 36 can be located at the waistband as shown in FIG. 10 to provide the garment with a reduced stress profile to reduce the appearance of the waistband through clothing. The width of the polymer film 36 can vary in the front or back of the garment to reduce pressure providing a pinch point or alter the stress profile to increase support (such as by providing tummy control). Similarly, the film portions at the leg bands 36 and 37 can vary in width to provide distribution of stress along the back portion decreasing a pinch point that can show as a panty line under clothing, such as by increasing the width of the film along the back portion 37. FIG. 11 includes a polymer film region 40 of a different geometry that can provide additional control, such as tummy control, or by providing support useful for maternity panties.

Figure 12:
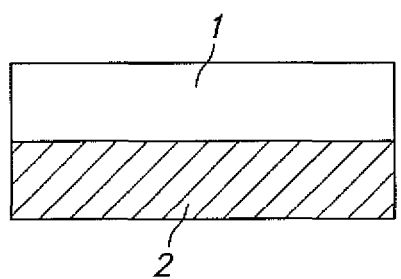
FIG. 12 shows a polymer film on a substrate.
Figure 13:
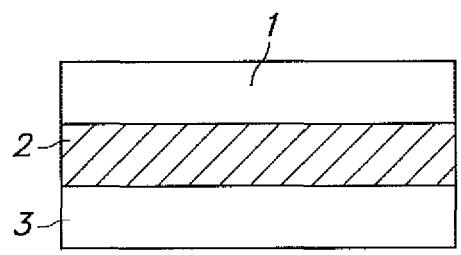
FIG. 13 shows a polymer film between two substrates.

Any of the polymer film regions 1 may be included on a single surface 2 as shown in FIG. 12 where the surface 2 may be either a fabric, foam or other substrate suitable for a garment. Alternatively, the polymer film 2 may be included between two surfaces such as a fabric, foam, etc. as in FIG. 13 where a top surface layer 1 and bottom surface layer 3 are included.

FIG. 14 and FIG. 15 show two possibilities for using a folded over fabric that provides a top surface layer 1 and a bottom surface layer 2 after folding along a preselected folding lines 42. Arrows show the direction of folding in FIG. 14 and FIG. 15. The edges of the bottom surface layers 3 meet to form a butt seam 5 as shown in FIG. 14A and FIG. 15A. The edges 5 may be attached or bonded to the film region 2 at that point.

FIG. 16 is a cross-section of a butt seam at line X-X as indicated in FIG. 14A. The seam 5 indicates the edges of the fabric or other substrate that is folded over and bonded or attached. The polymer film region 2 may be bonded to the top surface 1, the bottom surface 3 or two both the top and bottom surfaces. The folded portion 42 is indicated to demonstrate the orientation of layer prior to bonding, however, where the fabric is sufficiently thin, the cross-section will appear substantially linear. Also, a space 44 is shown to demonstrate that the bonded film 2 may not extend to the folded portion 42 of the fabric, however, this space 44 may be absent depending on the bonding technique because the film may melt and fill this available space.

Depending on the desired effect of the polyurethaneurea composition when applied as a film or dispersion from the aqueous dispersion described herein, the weight average molecular weight of the polymer in the film may vary from about 40,000 to about 150,000, including from about 100,000 to about 150,000 and about 120,000 to about 140,000.

In some embodiments, the polymer film may act as an adhesive to attach two or more layers of fabric or foam, or to attach a layer of fabric to foam. One suitable method for accomplishing this is to apply a dispersion to a layer by any suitable method. Methods for applying the dispersions of some embodiments include spraying, kissing, printing, brushing, dipping, padding, dispensing, metering, painting, and combinations thereof. This may be followed by application of heat and/or pressure.

The same methods for applying polyurethaneurea dispersion can be used for application of adhesive to attach a film to a fabric or foam layer. Examples of adhesives include thermoset or thermoplastic adhesives, pressure sensitive adhesives, hot melt adhesives, and combinations thereof. The adhesive may be used to adhere the different layers and may be applied to any of the fabric, foam or polyurethaneurea films or dispersion. Moreover, the polyurethaneurea aqueous dispersions may also be used as an adhesive to adhere more than one layer of any fabric, foam or polyurethaneurea film as described in some embodiments. Alternatively, the polymer film may be sewn into the garment.

As described above, there are a variety of fabric constructions that are useful for the articles of the present invention. Furthermore, the polyurethane composition may be either a film or a dispersion in any of these embodiments. In addition, the polyurethaneurea composition may provide structural properties, flexibility, adhesion, or any combination of these. The order of layer arrangement may be (1) fabric layer, foam layer, polyurethaneurea composition layer; (2) fabric layer, foam layer, polyurethaneurea composition layer, foam layer, fabric layer; (3) fabric layer, polyurethaneurea composition layer, fabric layer; (4) foam layer, polyurethaneurea layer, foam layer; (5) foam layer, polyurethaneurea composition layer; (6) fabric layer, polyurethaneurea layer; or any combination of these which may be combined to achieve more layers in the fabric construction. An adhesive may be included to adhere any of the layers, including wherein the polyurethaneurea composition is the adhesive.

A variety of different fibers and yarns may be used with the fabrics of some embodiments. These include cotton, wool, acrylic, polyamide (nylon), polyester, spandex, regenerated cellulose, rubber (natural or synthetic), bamboo, silk, soy or combinations thereof.

Aqueous polyurethane dispersions useful in some embodiments of the invention are provided from particular urethane prepolymers, which are described below in more detail.

Urethane prepolymers, or capped glycols, can generally be conceptualized as the reaction product of a polyol, a polyisocyanate, and a compound capable of salt-forming upon neutralization, before the prepolymer is dispersed in water and is chain-extended. Such prepolymers can typically be made in one or more steps, with or without solvents. Depending on whether the prepolymer is dissolved in a less volatile solvent (such as MEK, or NMP) which will remain in the dispersion; dissolved in a volatile solvent such as acetone, which can be later removed; or is dispersed in water without any solvent; the dispersion process can be classified in practice as the solvent process, acetone process, or prepolymer mixing process. The prepolymer mixing process has environmental and economical advantages, and therefore is also useful as the basic process for making the aqueous dispersions in the present invention.

In the prepolymer mixing process, it is important that the viscosity of the prepolymer is adequately low enough, without dilution by a solvent, to be transported and dispersed in water. The present invention in one embodiment, relates to polyurethane dispersions derived from such a prepolymer, which meet this viscosity requirement and do not have any organic solvent in the prepolymer or in the dispersion. In accordance with the invention, the prepolymer is the reaction product of a polyol (a), a diisocyanate (b) and a diol compound (c). However, prepolymers including an organic solvent are also contemplated.

The present invention can provide stable, aqueous polyurethane dispersions, which can be processed and applied directly as adhesive materials (i.e., without the need of any additional adhesive materials) for coating, bonding, and lamination to substrates by conventional techniques. Aqueous polyurethane dispersions falling within the scope of the present invention may be provided with or without the use of volatile organic materials; with acceptable curing time in production; and with good adhesion strength, heat resistance, and stretch/recovery properties in finished products and in practical applications.

Polyurethaneurea polymer films which may or may not be adhesive can be coated on a release paper, whereby aqueous dispersions of the can be used for bonding and lamination to substrates including textile fabrics. The adhesion can be activated by applying heat and/or pressure onto a substrate and the adhesive film with a residence time of less than one minute, for example, from about 15 seconds to about 60 seconds. The thus bonded articles have good stretch/recovery properties and are expected to be durable in normal wear and wash cycles.

Polyol components suitable as a starting material for preparing urethane prepolymers, according to the invention, are polyether glycols, polycarbonate glycols, and polyester glycols of number average molecular weight of about 600 to about 3,500.

Examples of polyether polyols that can be used include those glycols with two or more hydroxy groups, from ring-opening polymerization and/or copolymerization of ethylene oxide, propylene oxide, trimethylene oxide, tetrahydrofuran, and 3-methyltetrahydrofuran, or from condensation polymerization of a polyhydric alcohol, preferably a dial or dial mixtures, with less than 12 carbon atoms in each molecule, such as ethylene glycol, 1,3-propanediol, 1,4-butanediol, 1,5-pentanediol 1,6-hexanediol, neopentyl glycol, 3-methyl-1,5-pentanediol, 1,7-heptanediol, 1,8-octanediol, 1,9-nonanediol, 1,10-decanediol and 1,12-dodecanediol. A linear, bifunctional polyether polyol is preferred, and a poly(tetramethylene ether) glycol of molecular weight of about 1,700 to about 2,100, such as Terathane® 1800 (Invista) with a functionality of 2, is particularly preferred in the present invention.

Examples of polyester polyols that can be used include those ester glycols with two or more hydroxy groups, produced by condensation polymerization of aliphatic polycarboxylic acids and polyols, or their mixtures, of low molecular weights with no more than 12 carbon atoms in each molecule. Examples of suitable polycarboxylic acids are malonic acid, succinic acid, glutaric acid, adipic acid, pimelic acid, suberic acid, azelaic acid, sebacic acid, undecanedicarboxylic acid, and dodecanedicarboxylic acid. Examples of suitable polyols for preparing the polyester polyols are ethylene glycol, 1,3-propanediol, 1,4-butanediol, 1,5-pentanediol 1,6-hexanediol, neopentyl glycol, 3-methyl-1,5-pentanediol, 1,7-heptanediol, 1,8-octanediol, 1,9-nonanediol, 1,10-decanediol and 1,12-dodecanediol. A linear bifunctional polyester polyol with a melting temperature of about 5° C. to about 50° C. is preferred.

Examples of polycarbonate polyols that can be used include those carbonate glycols with two or more hydroxy groups, produced by condensation polymerization of phosgene, chloroformic acid ester, dialkyl carbonate or diallyl carbonate and aliphatic polyols, or their mixtures, of low molecular weights with no more than 12 carbon atoms in each molecule. Examples of suitable polyols for preparing the polycarbonate polyols are diethylene glycol, 1,3-propanediol, 1,4-butanediol, 1,5-pentanediol, 1,6-hexanediol, neopentyl glycol, 3-methyl-1,5-pentanediol, 1,7-heptanediol, 1,8-octanediol, 1,9-nonanediol, 1,10-decanediol and 1,12-dodecanediol. A linear, bifunctional polycarbonate polyol with a melting temperature of about 5° C. to about 50° C. is preferred.

The polyisocyanate component (b), suitable as another starting material for making urethane prepolymers according to the invention, can be an isomer mixture of diphenylmethane diisocyanate (MDI) containing 4,4'-methylene bis (phenyl isocyanate) and 2,4'-methylene bis(phenyl isocyanate) in the range of 4,4'-MDI to 2,4'-MDI isomer ratios of between about 65:35 to about 35:65, preferably in the range of about 55:45 to about 45:55 and more preferably at about 50:50. Examples of suitable polyisocyanate components include Mondur® ML (Bayer), Lupranate® MI (BASF), and Isonate® 50 O,P' (Dow Chemical).

Diol compounds (c), suitable as further starting materials for preparing urethane prepolymers according to the invention, include at least one diol compound with: (i) two hydroxy groups capable of reacting with the polyisocyanates b); and (ii) at least one carboxylic acid group capable of forming salt upon neutralization and incapable of reacting with the polyisocyanates (b). Typical examples of diol compounds (c) having a carboxylic acid group, include 2,2-dimethylopropionic acid (DMPA), 2,2-dimethylobutanoic acid, 2,2-dimethylovaleric acid, and DMPA initiated caprolactones such as CAPA® HC 1060 (Solvay). DMPA is preferred in the present invention.

The prepolymer can be prepared by mixing starting materials (a), (b), and (c) together in one step and by reacting at temperatures of about 50° C. to about 100° C. for adequate time until all hydroxy groups are essentially consumed and a desired % NCO of the isocyanate group is achieved. Alternatively, this prepolymer can be made in two steps by first reacting starting material (a) with excess (b), followed by reacting with component (c) until a final desired % NCO of the prepolymer is achieved. For example, the % NCO may range from about 1.3 to about 6.5, such as from about 1.8 to about 2.6. Significantly, no organic solvent is added to or mixed with the starting materials before, during or after the reaction. Optionally, a catalyst may be used to facilitate the prepolymer formation.

In an embodiment of the present invention, the prepolymer comprises components (a), (b), and (c), which are combined together and provided in the following ranges of weight percentages, based on the total weight of the prepolymer:
about 34% to about 89% of component (a);
about 59% to about 10% of component (b); and
about 7.0% to about 1.0% of component (c).

In another embodiment of present invention, the prepolymer comprises Terathane® 1800 polyether glycol as component (a), Mondur® ML diisocyanate as component (b), and 2,2-dimethylopropionic acid (DMPA) as component (c). Within such embodiments, these components may, for example, be present in the following ranges of weight percentages, based on the total weight of the prepolymer:
a) Terathane® 1800 polyether glycol: about 61% to about 80%;
b) Mondur® ML diisocyanate: about 35% to about 18%; and
c) 2,2-dimethylopropionic acid (DMPA): about 4.0% to about 2.0%.

The prepolymer prepared from components (a), (b) and (c) may have a bulk viscosity (without any solvent present) below about 6,000 poises, such as below about 4,500 poises, measured by the falling ball method at 40° C. This prepolymer, containing carboxylic acid groups along the polymer chains, can be dispersed with a high-speed disperser into a de-ionized water medium that comprises: at least one neutralizing agent (d), to form an ionic salt with the acid; at least one surface active agent (ionic and/or non-ionic dispersant or surfactant); and, optionally, at least one diamine chain extension component (f). Alternatively, the neutralizing agent can be mixed with the prepolymer before being dispersed into the water medium. At least one antifoam and/or defoam agent and preferably at least one rheological modifier can be added to the water medium before, during, or after the prepolymer is dispersed.

Examples of suitable neutralizing agents (d) to convert the acid groups to salt groups include: tertiary amines (such as triethylamine, N,N-diethylmethylamine, N-methylmorpholine, N,N-diisopropylethylamine, and triethanolamine) and alkali metal hydroxides (such as lithium, sodium and potassium hydroxides). Primary and/or secondary amines may be also used as the neutralizing agent for the acid groups. The degrees of neutralization are generally between about 60% to about 140%, for example, in the range of about 80% to about 120% of the acid groups.

Examples of suitable diamine chain extenders (f) include: 1,2-ethylenediamine, 1,4-butanediamine, 1,6-hexamethylenediamine, 1,12-dodecanediamine, 1,2-propanediamine, 2-methyl-1,5-pentanediamine, 1,2-cyclohexanediamine, 1,4-cyclohexanediamine, 4,4'-methylene-bis(cyclohexylamine), isophorone diamine, 2,2-dimethyl-1,3-propanediamine, meta-tetramethylxylenediamine, and Jeffamine® (Texaco) of molecular weight less than 500.

Examples of suitable surface active agents include: anionic, cationic, or nonionic dispersants or surfactants, such as sodium dodecyl sulfate, sodium dodecylbenzenesulfonate, ethoxylated nonylphenols, and lauryl pyridinium bromide.

Examples of suitable antifoaming or deforming or foam controlling agents include: Additive 65 and Additive 62 (silicone based additives from Dow Corning), FoamStar® 1300 (a mineral oil based, silicone free defoamer from Cognis) and Surfynol™ DF 110L (a high molecular weight acetylenic glycol non-ionic surfactant from Air Products & Chemicals).

Examples of suitable rheological modifiers include: hydrophobically-modified ethoxylate urethanes (HEUR), hydrophobically-modified alkali swellable emulsions (HASE), and hydrophobically-modified hydroxy-ethyl cellulose (HMHEC).

At least one monofunctional dialkyl amine compound or monofunctional alcohol, as the blocking agent (e) for isocyanate groups, may be added to the water medium during or after the prepolymer is dispersed to control the weight average molecular weight of the polyurethaneurea polymer. For example, the blocking agent can be added to the water mixture immediately after the prepolymer is dispersed. Optionally at least one polymeric component (g) (MW> about 500), with at least three or more primary and/or secondary amino groups per mole of the polymer, is added to the water medium after the prepolymer is dispersed and the blocking agent is added.

Examples of suitable mono-functional dialkylamine blocking agents (e) include: N,N-diethylamine, N-ethyl-N-propylamine, N,N-diisopropylamine, N-tert-butyl-N-methylamine, N-tert-butyl-N-benzylamine, N,N-dicyclohexylamine, N-ethyl-N-isopropylamine, N-tert-butyl-N-isopropylamine, N-isopropyl-N-cyclohexylamine, N-ethyl-N-cyclohexylamine, N,N-diethanolamine, and 2,2,6,6-tetramethylpiperidine. The molar ratio of the amine blocking agent to the isocyanate groups of the prepolymer prior to dispersion in water generally should range from about 0.05 to about 0.50, for example from about 0.20 to about 0.40. Catalysts may be used for the de-blocking reactions.

Examples of monofunctional alcohol blocking agents (e) include: aliphatic and cycloaliphatic primary and secondary alcohols with 1 to 18 carbons, phenol, substituted phenols, ethoxylated alkyl phenols and ethoxylated fatty alcohols with molecular weight less than about 750, including molecular weight less than 500, hydroxyamines, hydroxymethyl and hydroxyethyl substituted tertiary amines, hydroxymethyl and hydroxyethyl substituted heterocyclic compounds, and combinations thereof, including furfuryl alcohol, tetrahydrofurfuryl alcohol, N-(2-hydroxyethyl)succinimide, 4-(2-hydroxyethyl)morpholine, methanol, ethanol, butanol, neopentyl alcohol, hexanol, cyclohexanol, cyclohexanemethanol, benzyl alcohol, octanol, octadecanol, N,N-diethylhydroxylamine, 2-(diethylamino)ethanol, 2-dimethylaminoethanol, and 4-piperidineethanol, and combinations thereof.

Examples of the suitable polymeric component (g) include: polyethylenimine, poly(vinylamine), poly(allylamine), and poly(amidoamine) dendrimers.

An anti-yellowing compound useful in some polyurethaneurea dispersions includes an aliphatic or aromatic isocyanate (mono-functional), an aliphatic diisocyanate, or a combination thereof.

Examples of anti-yellowing monoisocyanates include aliphatic monoisocyanates, cycloaliphatic isocyanates. Specifically included are compounds of the formula R—N=C=O, where are is aliphatic or cylcoaliphatic such as ethyl-, propyl-, butyl-, pentyl-, hexyl, cyclohexyl-, etc. as well as aromatic monoisocyanates. Aliphatic polyisocyanates have been used in polyurethane applications to reduce yellowing due to the absence of an aromatic group. In the present invention, a monoisocyanate is added to a polyurethaneurea dispersion prepared with an aromatic polyisocyanate and surprisingly results in a composition that has a significant reduction in yellowing of films cast and dried from the dispersion. Yellowing can result from exposure to environmental or process conditions such as heat, NO2, and UV, among others.

A non-limiting list of suitable monoisocyanates include: 1-methyl-decyl isocyanate, 2-chloroethyl isocyanate, 2-ethylhexyl isocyanate, 2-methylcyclohexyl isocyanate, 3-(triethoxysilyl)propyl isocyanate, 3-chloropropyl isocyanate, 3-isopropenyl-a,a-dimethylbenzyl isocyanate, 3-methylcyclohexyl isocyanate, 4-methycyclohexyl isocyanate, 6-chlorohexyl isocyanate, benzyl isocyanate, cycloheptyl isocyanate, cycloheptyl isocyanate, cyclohexyl isocyanate, cyclohexanemethyl isocyanate, cyclooctyl isocyanate, decyl isocyanate, dodecyl isocyanate, isocyanatoacetic acid n-butyl ester, isopropyl isocyanate, n-hepyl isocyanate, n-hexyl isocyanate, nonyl isocyanate, octadecyl isocyanate, octyl isocyanate, pentyl isocyanate, phenethyl isocyanate, trans-4-methycyclohexyl isocyanate, α-methylbenzyl isocyanate, (3-isocyanatopropyl)triethoxysilane, ethyl 6-isocyanatohexanoate, ethyl 3-isocyanatopropionate, 1-tetradecyl isocyanate, and combinations thereof. An example of a suitable aromatic monoisocyanate includes phenyl isocyanate, which may be used alone or in combination with other aromatic or aliphatic isocyanates.

A variety of different aliphatic diisocyanates are also useful as anti-yellowing compounds and may be used alone, or in combinations with other aliphatic diisocyanates or a monoisocyanate.

Other additives that may be optionally included in the aqueous dispersion or in the prepolymer include: antioxidants, UV stabilizers, colorants, pigments, crosslinking agents, phase change materials (i.e., Outlast®, commercially available from Outlast Technologies, Boulder, Colo.), antimicrobials, minerals (i.e., copper), microencapsulated well-being additives (i.e., aloe vera, vitamin E gel, aloe vera, sea kelp, nicotine, caffeine, scents or aromas), nanoparticles (i.e., silica or carbon), calcium carbonate, flame retardants, antitack additives, chlorine degradation resistant additives, vitamins, medicines, fragrances, electrically conductive additives, and/or dye-assist agents (i.e., Methacrol®, commercially available from E.I. DuPont de Nemours, Wilmington, Del.). Other additives which may be added to the prepolymer or the aqueous dispersion comprise adhesion promoters, anti-static agents, anti-cratering agents, anti-crawling agents, optical brighteners, coalescing agents, electroconductive additives, luminescent additives, flow and leveling agents, freeze-thaw stabilizers, lubricants, organic and inorganic fillers, preservatives, texturizing agents, thermochromic additives, insect repellants, and wetting agents.

Such optional additives may be added to the aqueous dispersion before, during, or after the prepolymer is dispersed, as the process allows. No organic solvent is added to the aqueous dispersion at any time.

Polyurethane aqueous dispersions falling within the scope of the present invention should be expected to have a solids content of from about 10% to about 50% by weight, for example from about 30% to about 45% by weight. The viscosity of polyurethane aqueous dispersions falling within the scope of the present invention may be varied in a broad range from about 10 centipoises to about 100,000 centipoises depending on the processing and application requirements. For example, in one embodiment, the viscosity is in the range of about 500 centipoises to about 30,000 centipoises. The viscosity may be varied by using an appropriate amount of thickening agent, such as from about 0 to about 2.0 wt %, based on the total weight of the aqueous dispersion.

An organic solvent may also be used in the preparation of films and dispersions of some embodiments. The organic solvent may be used to lower the prepolymer viscosity through dissolution and dilution and/or to assist the dispersion of solid particles of the dial compound having a carboxylic acid group such as 2,2-dimethylopropionic acid (DMPA) to enhance the dispersion quality. It may also serve for the purposes to improve the film uniformity such as reducing streaks and cracks in the coating process.

The solvents selected for these purposes are substantially or completely non-reactive to isocyanate groups, stable in water, and have a good solubilizing ability for DMPA, the formed salt of DMPA and triethylamine, and the prepolymer. Examples of suitable solvents include N-methylpyrrolidone, N-ethylpyrrolidone, dipropylene glycol dimethyl ether, propylene glycol n-butyl ether acetate, N,N-dimethylacetamide, N,N-dimethylformamide, 2-propanone (acetone) and 2-butanone (methylethylketone or MEK).

The amount of solvent added to the films/dispersion of some embodiments may vary. When a solvent is include, suitable ranges of solvent include amounts of less than 50% by weight of the dispersion. Smaller amounts may also be used such as less than 20% by weight of the dispersion, less than 10% by weight of the dispersion, less than 5% by weight of the dispersion and less than 3% by weight of the dispersion.

There are many ways to incorporate the organic solvent into the dispersion at different stages of the manufacturing process, for example,
1) The solvent can be added to and mixed with the prepolymer after the polymerization is completed prior to transferring and dispersing the prepolymer, the diluted prepolymer containing the carboxylic acid groups in the backbone and isocyanate groups at the chain ends is neutralized and chain extended while it is dispersed in water.
2) The solvent can be added and mixed with other ingredients such as Terathane® 1800, DMPA and Lupranate® MI to make a prepolymer in the solution, and then this prepolymer containing the carboxylic acid groups in the backbone and isocyanate groups at the chain ends in the solution is dispersed in water and at the same time it is neutralized and chain extended.
3) The solvent can be added with the neutralized salt of DMPA and Triethylamine (TEA), and mixed with Terathane® 1800 and Lupranate® MI to make the prepolymer prior to dispersion.
4) The solvent can be mixed with TEA, and then added to the formed prepolymer prior to dispersion.
5) The solvent can be added and mixed with the glycol, followed by the addition of DMPA, TEA and then Lupranate® MI in sequence to a neutralized prepolymer in solution prior to dispersion.

The aqueous polyurethane dispersions of the some embodiments are particularly suitable for adhesive polymer films, which can be used for fabric bonding, lamination, and adhesion purposes when applied with heat and pressure for a relatively short period of time Pressures, can for example, range from about atmospheric pressure to about 60 psi and times can range from less than about one second to about 30 minutes in accordance with the bonding method used.

Such polymer films may be made by coating the dispersion onto a release paper and drying to remove water at temperatures below about 100° C. through commercially available processes to form a film on the paper. The formed film sheets can be slit into strips of desired width and wound-up into spools for later use in applications to form stretch articles, for example textile fabrics. Examples of such applications include: stitch-less or seamless garment constructions; seam seal and reinforcement; labels and patches bonding to garments; and localized stretch/recovery enhancement. The adhesion bonding can be developed in the temperature range of from about 100° C. to about 200° C., such as from about 130° C. to about 200° C., for example, from about 140° C. to about 180° C., in a period of 0.1 seconds to several minutes, for example, less than about one minute. Typical bonding machines are Sew Free (commercially available from SewSystems in Leicester, England), Macpi hemming machine (commercially available from the Macpi Group in Brescia, Italy), Framis hot air welding machine (commercially available from Framis Italy, s p.a. in Milano, Italy). This bonding is expected to be strong and durable when exposed to repeated wear, wash, and stretch in a textile fabric garment.

The coating, dispersion, or shaped article may be pigmented or colored and also may be used as a design element in that regard.

In addition, articles with laminated films or dispersions can be molded. For example, fabric can be molded under conditions appropriate for the hard yarn in the fabric. Also, molding may be possible at temperature which will mold the shaped article or dispersion, but below temperatures suitable for molding the hard yarn.

One suitable method of attaching a layer of polymer film to a substrate is lamination using any method wherein heat or energy is applied to the laminate surface. Methods of heat application include, for example, ultrasonic, direct heat, indirect heat, and microwave. Such direct lamination may provide an advantage in view of other methods used in the art in that the shaped article may not only bond to the a substrate via a mechanical interaction but also via a chemical bond. For example, if the substrate has any reactive hydrogen functional groups, such groups may react with the isocyanate and hydroxyl groups on the dispersion or shaped article, thereby providing a chemical bond between the substrate and the dispersion or shaped article. Such chemical bonding of the dispersion or shaped article to the substrate can give a much stronger bond. Such bonding may occur in dry polymer films that are cured onto a substrate or in wet dispersions that are dried and cured in one step. Materials without an active hydrogen include polypropylene fabrics and anything with a fluoropolymer or a silicone based surface. Materials with an active hydrogen include, for example, nylon, cotton, polyester, wool, silk, cellulosics, acetates, metals, and acrylics. Additionally, articles treated with acid, plasma, or another form of etching may have active hydrogens for adhesion. Dye molecules also may have active hydrogens for bonding.

Methods and means for applying the polymer films of some embodiments include, but are not limited to: roll coating (including reverse roll coating); use of a metal tool or knife blade (for example, pouring a dispersion onto a substrate and then casting the dispersion into uniform thickness by spreading it across the substrate using a metal tool, such as a knife blade); spraying (for example, using a pump spray bottle); dipping; painting; printing; stamping; and impregnating the article. These methods can be used to apply dispersion directly onto a substrate without the need of further adhesive materials and can be repeated if additional/heavier layers are required. The dispersions can be applied to any fabrics of knits, wovens or nonwovens made from synthetic, natural, or synthetic/natural blended materials for coating, bonding, lamination and adhesion purposes. The water in the dispersion can be eliminated with drying during the processing (for example, via air drying or use of an oven), leaving the precipitated and coalesced polyurethane layer on the fabrics to form an adhesive bond.

At least one coagulant may optionally be used to control or to minimize penetration of dispersions according to the invention into a fabric or other article. Examples of coagulants that may be used include calcium nitrate (including calcium nitrate tetrahydrate), calcium chloride, aluminum sulfate (hydrated), magnesium acetate, zinc chloride (hydrated) and zinc nitrate.

An example of a tool that can be used for applying dispersions is a knife blade. The knife blade can be made of metal or any other suitable material. The knife blade can have a gap of a predetermined width and thickness. The gap may range in thickness, for example, from 0.2 mils to 50 mils, such as a thickness of 5 mils, 10 mils, 15 mils, 25 mils, 30 mils, or 45 mils.

The thickness of the films, solutions, and dispersions may vary depending on the application. In the case of dry polymer films, the final thickness may, for example, range from about 0.1 mil to about 250 mil, such as from about 0.5 mil to about 25 mil, including from about 1 to about 6 mil (one mil=one thousandth of an inch).

Suitable thicknesses include about 0.5 mil to about 12 mil, about 0.5 to about 10 mil, and about 1.5 mil to about 9 mil. For aqueous dispersions, the amount used may, for example, range from about 2.5 g/m² to about 6.40 kg/m², such as from about 12.7 to about 635 g/m², including from about 25.4 to about 152.4 g/m².

Types of planar sheets and tapes that can be coated with dispersions and polymer films falling within the scope of the present invention include, but are not limited to: textile fabrics, including wovens and knits; nonwovens; leather (real or synthetic); paper; metal; plastic; and scrim.

End articles that can be produced using the dispersions and polymer films falling within the scope of the present invention include, but are not limited to: apparel, which includes any type of garment or article of clothing; knitted gloves; upholstery; hair accessories; bed sheets; carpet and carpet backing; conveyor belts; medical applications, such as stretch bandages; personal care items, including incontinence and feminine hygiene products; and footwear. Articles coated with dispersion or covered with film or tape may be used as sound suppression articles.

Non-elastic fabrics laminated to polymer films can have improved stretch and recovery and improved molding properties.

Articles including polymer films, film, tape, or aqueous polyurethane dispersion may be molded. The articles may be made with multiple layers of substrate and shaped article, film, tape, or dispersion. The multi-layered articles also may be molded. Molded and non-molded articles may have different levels of stretch and recovery. The molded articles may comprise a body shaping or body supporting garment, such as a brassiere.

Examples of apparel or garments that can be produced using dispersions and polymer films, include but are not limited to: undergarments, brassieres, panties, lingerie, swimwear, shapers, camisoles, hosiery, sleepwear, aprons, wetsuits, ties, scrubs, space suits, uniforms, hats, garters, sweatbands, belts, activewear, outerwear, rainwear, cold-weather jackets, pants, shillings, dresses, blouses, mens and womens tops, sweaters, corsets, vests, knickers, socks, knee highs, dresses, blouses, aprons, tuxedos, bisht, abaya, hijab, jilbab, thoub, burka, cape, costumes, diving suit, kilt, kimono, jerseys, gowns, protective clothing, sari, sarong, skirts, spats, stola, suits, straitjacket, toga, tights, towel, uniform, veils, wetsuit, medical compression garments, bandages, suit interlinings, waistbands, and all components therein.

The following examples are meant to be exemplary and not limiting of the embodiments described herein.

Included below are examples of polymer films that are useful in the articles of some embodiments. Testing including inventive and comparative examples are also included.

EXAMPLES

Terathane® 1800 is a linear polytetramethylene ether glycol (PTMEG), with a number average molecular weight of 1,800 (commercially available from INVISTA S.à. r.L., of Wichita, Kans.);

Pluracol® HP 4000D is a linear, primary hydroxyl terminated polypropylene ether glycol, with a number average molecular weight of 400 (commercially available from BASF, Bruxelles, Belgium);

Mondur® ML is an isomer mixture of diphenylmethane diisocyanate (MDI) containing 50-60% 2,4'-MDI isomer and 50-40% 4,4'-MDI isomer (commercially available from Bayer, Baytown, Tex.);

Lupranate® MI is an isomer mixture of diphenylmethane diisocyanate (MDI) containing 45-55% 2,4'-MDI isomer and 55-45% 4,4'-MDI isomer (commercially available from BASF, Wyandotte, Mich.);

Isonate® 125 MDR is a pure mixture of diphenylmethane diisocyanate (MDI) containing 98% 4,4'-MDI isomer and 2% 2,4'-MDI isomer (commercially available from the Dow Company, Midland, Mich.); and DMPA is 2,2-dimethylopropionic acid.

The following prepolymer samples were prepared with MDI isomer mixtures, such as Lupranate® MI and Mondur® ML, containing a high level of 2,4'-MDI.

Example 1

The preparation of the prepolymers was conducted in a glove box with nitrogen atmosphere. A 2000 ml Pyrex® glass reaction kettle, which was equipped with an air pressure driven stirrer, a heating mantle, and a thermocouple temperature measurement, was charged with about 382.5 grams of Terathane® 1800 glycol and about 12.5 grams of DMPA. This mixture was heated to about 50° C. with stirring, followed by the addition of about 105 grams of Lupranate® MI diisocyanate. The reaction mixture was then heated to about 90° C. with continuous stirring and held at about 90° C. for about 120 minutes, after which time the reaction was completed, as the % NCO of the mixture declined to a stable value, matching the calculated value (% NCO aim of 1.914) of the prepolymer with isocyanate end groups. The viscosity of the prepolymer was determined in accordance with the general method of ASTM D1343-69 using a Model DV-8 Falling Ball Viscometer (sold by Duratech Corp., Waynesboro, Va.) operated at about 40° C. The total isocyanate moiety content, in terms of the weight percent of NCO groups, of the capped glycol prepolymer was measured by the method of S. Siggia, "Quantitative Organic Analysis via Functional Group", 3rd Edition, Wiley & Sons, New York, pp. 559-561 (1963), the entire disclosure of which is incorporated herein by reference.

Example 2

The solvent-free prepolymer, as prepared according to the procedures and composition described in Example 1, was used to make a polyurethaneurea aqueous dispersion.

A 2,000 ml stainless steel beaker was charged with about 700 grams of de-ionized water, about 15 grams of sodium dodecylbenzenesulfonate (SDBS), and about 10 grams of triethylamine (TEA). This mixture was then cooled with ice/water to about 5° C. and mixed with a high shear laboratory mixer with rotor/stator mix head (Ross, Model 100LC) at about 5,000 rpm for about 30 seconds. The viscous prepolymer, prepared in the manner as Example 1 and contained in a metal tubular cylinder, was added to the bottom of the mix head in the aqueous solution through flexible tubing with applied air pressure. The temperature of the prepolymer was maintained between about 50° C. and about 70° C. The extruded prepolymer stream was dispersed and chain-extended with water under the continuous mixing of about 5,000 rpm. In a period of about 50 minutes, a total amount of about 540 grams of prepolymer was introduced and dispersed in water. Immediately after the prepolymer was added and dispersed, the dispersed mixture was charged with about 2 grams of Additive 65 (commercially available from Dow Corning®, Midland Mich.) and about 6 grams of diethylamine (DEA). The reaction mixture was then mixed for about another 30 minutes. The resulting solvent-free aqueous dispersion was milky white and stable. The viscosity of the dispersion was adjusted with the addition and mixing of Hauthane HA thickening agent 900 (commercially available from Hauthway, Lynn, Mass.) at a level of about 2.0 wt % of the aqueous dispersion. The viscous dispersion was then filtered through a 40 micron Bendix metal mesh filter and stored at room temperatures for film casting or lamination uses. The dispersion had solids level of 43% and a viscosity of about 25,000 centipoises. The cast film from this dispersion was soft, tacky, and elastomeric.

Example 3

The preparation procedures were the same as Example 2, except that DEA was not added into the dispersion after the prepolymer was mixed. Initially, the dispersion appeared to be no different from Example 2.

Example 4

Fabric Including Various Laminated Films were Subjected to Stress/Strain Testing Elongation and tenacity properties were measured on films using a dynamic tensile tester Instron. The sample size was as indicated below. The sample was placed in clamps and extended at a strain rate of 200% elongation per minute until a maximum elongation was reached. The tenacity and elongation were measured just prior to the film break. Similarly, the set % was measured by extending a laminated sample from 0 to 50% elongation for five cycles at a strain rate of 200% per minute. The set % was measured after the fourth cycle.

The films of Samples A and B are polyurethaneurea films cast from the dispersion of Example 3. The films of Samples D, K, L, and M were polyurethaneurea films cast from the dispersion of Example 2. The films of Samples C, G, H, I, and J were three-layered polyurethaneurea "sandwich" films cast from the dispersion of Example 3, with a film from the dispersion of Example 2 on each side. The film of Sample E and nonwoven of Sample F were prepared from a polypropylene based polymer commercially available from Exxon-Mobil under the trade name VISTAMAXX. Sample N was a comparative example using a hot melt glue in a dot matrix configuration.

Using Pacific Fabric a range of tape (narrow strip) and film variants were bonded to fabric. The conditions for preparation of Samples are described in Table 1 below. Each fabric/polymer composition sample had a width of 63.5 mm.

TABLE 1

| Sample | Polymer Composition Description | Press Temp ° C. | Press Time (sec) | Press Pressure (bar) |
|---|---|---|---|---|
| A | Film 3 mil thick | 200 | 30 | 5 |
| B | Film 1.5 mil thick | 200 | 30 | 5 |
| C | Film 7 mil thick | 170 | 45 | 5 |
| D | 2 Films 2 mil thick | 170 | 45 | 5 |
| E | Film 3 mil thick | 170 | 45 | 5 |
| F | Nonwoven 60 oz/yd² | 170 | 45 | 5 |
| G | Film 7 mil thick | 170 | 45 | 5 |
| H | Film 7 mil thick including 11 side-by side pieces of approximately equal width | 170 | 45 | 5 |
| I | Film 7 mil thick | 170 | 45 | 5 |
| J | Film 7 mil thick | 170 | 45 | 5 |
| K | Film 4 mil thick | 170 | 45 | 5 |
| L | Film 4 mil thick | 170 | 45 | 5 |
| M | Film 4 mil thick | 170 | 45 | 5 |
| N | Dot matrix | 150 | 30 | 5 |

Figure 17:
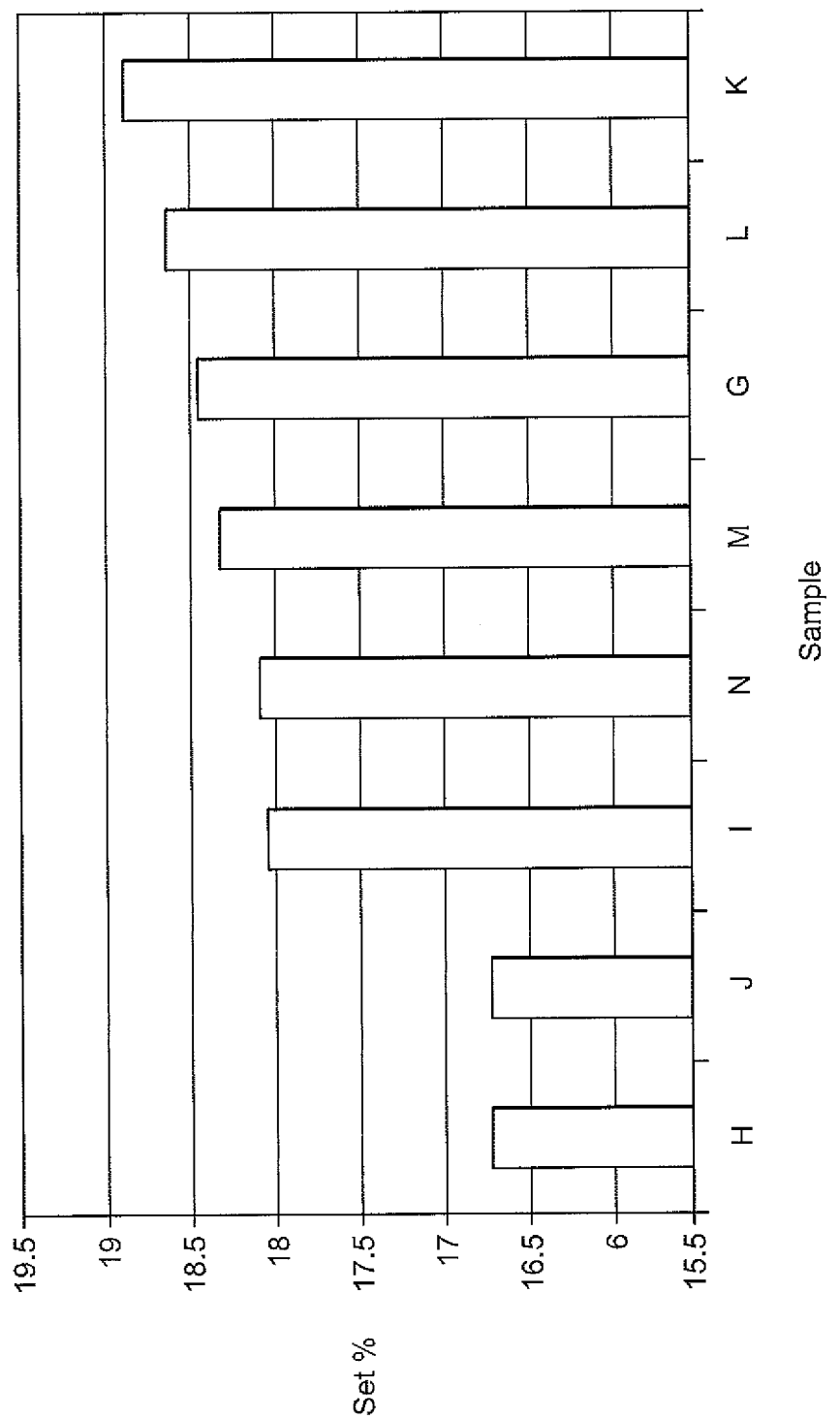
FIG. 17 is a graphic representation of the set % of garments laminated with polymer compositions.
Figure 19:
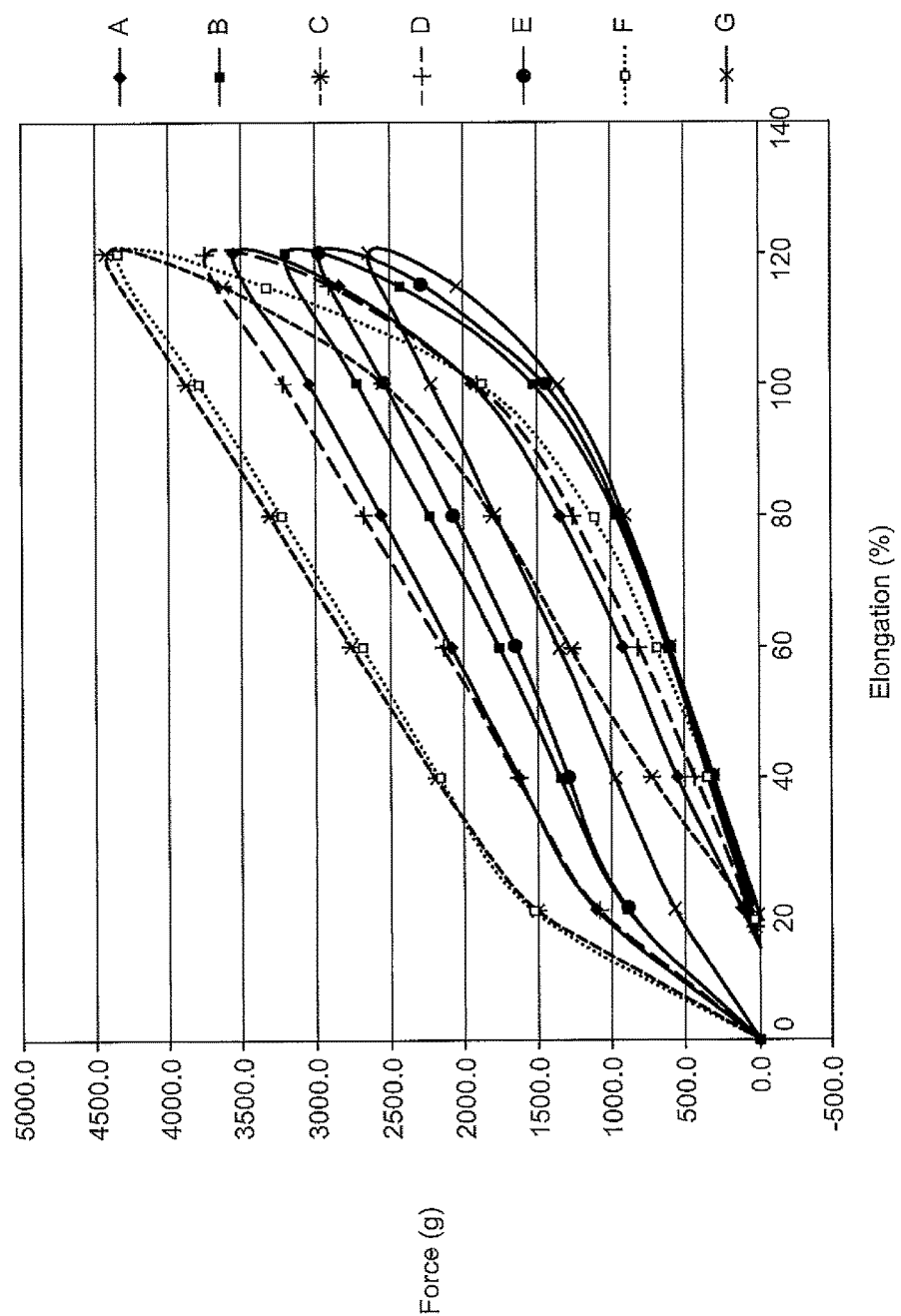
FIG. 19 is a graphic representation of a stress/strain analysis.
Figure 20:
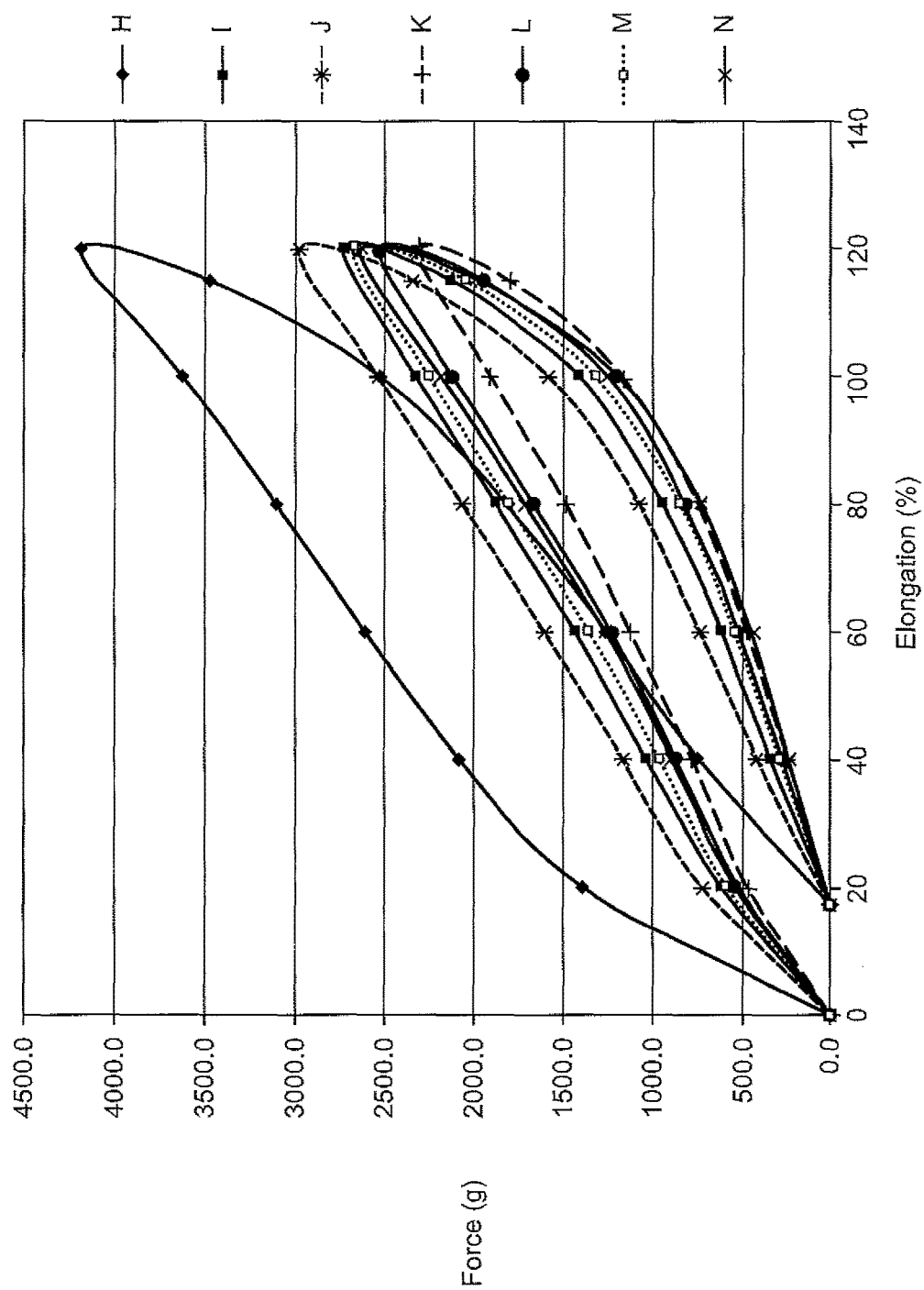
FIG. 20 is a graphic representation of a stress/strain analysis

These samples were tested in Instron cycling to 120% elongation, 3 times and measuring the elongation (set) on the fourth load at 25 gram force (as shown in FIG. 17). The first cycle data is shown in FIG. 19 for samples A-G and in FIG. 20 for samples H-N as shown in FIG. 17. By evaluating this data one can see that the stress/strain behavior of the base fabric can be enhanced by the application of the polyurethaneurea films prepared from the dispersions of Examples 2 and 3. The films add power, particularly the samples include films of Example 3 (A, B, C, G, H, I, and J). The set data suggests that when compared to a stretch narrow bra wing the laminated wings using films including the composition of Example 3 can give comparable recovery (set) and power (load/unload). The laminated wings including the composition of Example 3 can offer improved performance vs. commercial bra wings of laminated fabrics/foam constructions.

Example 5

To demonstrate effect of altering stress profile of a garment, a commercially available bra was retrofit with a range of film and narrow film/tape variants as shown in Table 2. These film/tape variants were applied to the bra wing which has a substantially trapezoidal shape. The commercially available bra was Victoria's Secret: Secret Embrace Style 6505, size 36 C. These garments were fit and wear tested.

The polymer composition of Test 12 was a polyurethaneurea film cast and dried from the dispersion of Example 2. The polymer composition of Tests 2, 3, 7, 9-11, 13 and 21 were polyurethaneurea films cast and dried from the dispersion of Example 3. Tests 1, 4-7, 15, 18, and 19 include three-layered polyurethaneurea "sandwich" films cast from the dispersion of Example 3, with a film from the dispersion of Example 2 on each side. Test 8 is the control including no retrofit polymer composition. Tests 14 and 20 include a polyurethane film commercially available from Bemis (Bemis 3410). The film of Test 16 and the nonwoven of Test 17 were prepared from a polypropylene based polymer commercially available from ExxonMobil under the trade name VISTAMAXX.

TABLE 2

Retrofit of Commercial Bra

| Test | Description of Modification | Polymer Composition Description | Temp ° C. | Time (sec) | Pressure (bar) |
|---|---|---|---|---|---|
| 1 | Tape along edge | 8 mm width, 7 mil thick | 175 | 45 | 5 |
| 2 | Cover entire wing | 1.5 mil thick | 200 | 30 | 5 |
| 3 | Cover entire wing | 3 mil thick | 175 | 45 | 5 |
| 4 | Tape along edge | 6 mm width, 7 mil thick | 175 | 45 | 5 |
| 5 | Tape along edge | 8 mm width, 7 mil thick | 175 | 45 | 5 |
| 6 | Tape along edge | 10 mm width, 7 mil thick | 175 | 45 | 5 |
| 7 | Cover entire wing | 1.5 mil thick | 200 | 30 | 5 |
| 8 | Control | None | 165 | 45 | 5 |
| 9 | Tape along edge | 6 mm width, 6 mil thick | 200 | 30 | 5 |
| 10 | Trapezoid shape according to FIG. 1 with edges 4 folded over and bonded | 1.5 mil thick | 175 | 45 | 5 |
| 11 | Trapezoid shape of wing folded in half and reversed 180° | 3 mil thick | 175 | 45 | 5 |
| 12 | Two film layers covering entire wing | 4 mil thick | 175 | 45 | 5 |
| 13 | Trapezoid shape covering entire wing | 1.5 mil thick | 175 | 45 | 5 |
| 14 | Trapezoid shape covering entire wing | 2 mil thick | 165 | 45 | 5 |
| 15 | Narrow film applied according to FIG. 3 | 7 mil thick | 175 | 45 | 5 |
| 16 | Trapezoid shape covering entire wing | 4 mil thick | 165 | 45 | 5 |
| 17 | Trapezoid shape covering entire wing | Nonwoven 90 oz/yd$^2$ | 165 | 45 | 5 |
| 18 | Narrow film applied according to FIG. 3 | 7 mil thick | 150 | 45 | 5 |
| 19 | Film bonded to edges | 7 mil thick | 150 | 45 | 5 |
| 20 | Film bonded to edges | 2 mil thick | 150 | 45 | 5 |
| 21 | Film bonded to edges | 3 mil thick | 175 | 45 | 5 |

Figure 18:
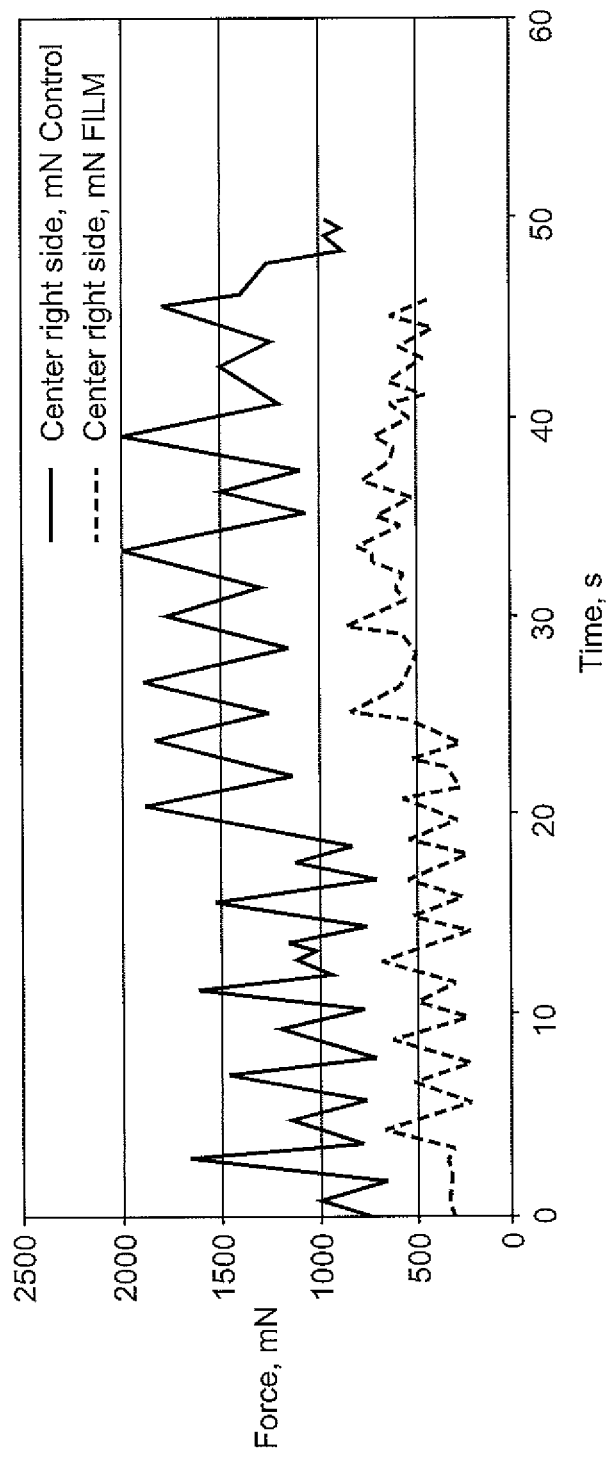
FIG. 18 is a graphic representation of a control fabric compared to a polymer film.

The film of Test 3 and Test 8 (control) were compared for compression force measured with Gebiom Dynamic Force Sensor. Measurements were taken in the center of the bra wing where the film had been bonded to the garment. Results are shown in FIG. 18. By comparing the force of the control garment versus the garment with the film in Test 3 bonded to it, concluded that adding this film provided about 3× the compressive force of garment alone. From this, it was extrapolated that a film of similar composition having a half the thickness would result in a compressive force approximately equal to that of the garment alone. While it would be expected that the film would result in a compressive force approximately equal to that of 2× the garment alone.

Using this information, the intent was to construct a garment in which along the length of the bra wing would result an equal compressive force on the body. The bra wing is essentially a trapezoid shape, as shown in FIGS. 1 to 3.

Since the bra wing is wider at the front (where it is attached to the bra) than the back (where it is attached to a hook or eye closure), the front of the bra wing will have a higher force when worn at equal elongation. To improve the comfort, an inverted trapezoid of polyurethaneurea film of 1.5 mil thickness (Test 10) was applied by bonding to the bra wing trapezoid as shown in the FIG. 1.

Similarly, Test 11 was made using an inverted trapezoid of 3 mil thick polyurethaneurea film of Example 3 bonded to the bra wing trapezoid, except that the trapezoid was cut in half along the length, since the 3 mil thick film has 2× the compressive force of the bra wing.

Test 18, was prepared using a tape of 10 mm wide film. This was bonded diagonally from the bottom of the cup to the top of the hook/eye closure, as shown in FIG. 3. This provided a means to uplift, improve the comfort and fit of the bra by engineered design and placement of the increased power and recovery.

The resultant bras were fit and wear tested. The improved comfort and fit was validated by the fit model for the retrofit bras of Tests 10, 11, and 18.

While the present invention has been described in an illustrative manner, it should be understood that the terminology used is intended to be in a nature of words or description rather than of limitation. Furthermore, while the present invention has been described in terms of several illustrative embodiments, it is to be appreciated that those skilled in the art will readily apply these teachings to other possible variations of the invention.

What is claimed is:

1. A body shaping garment comprising:
    (a) one or more sections of fabric, wherein each section of fabric has an initial stress profile; and
    (b) one or more polymeric dispersions adhered to said one or more sections of fabric to form one or more laminate section(s);
    wherein the one or more polymeric dispersions is trapezoidal or triangular in shape and is geometrically inverted in the fabric or is a narrow strip oriented along a diagonal to the fabric and
    wherein the stress profile of the one or more laminate section(s) is altered from said initial stress profile of said one or more sections of fabric to provide comfort to the body shaping garment by distributing stress throughout the body shaping garment and/or avoiding pinch points while increasing stress in portions of the body shaping garment to provide additional control and support.

2. The body shaping garment of claim 1, wherein said different stress profile provides a stress and/or pressure gradient to provide additional support at one or more areas within said fabric laminate.

3. The body shaping garment of claim 2, wherein the different stress profile provides a performance enhancing property.

4. The body shaping garment of claim 1, wherein said fabric has a construction selected from the group consisting of single and multiple layers.

5. The body shaping garment of claim 4, wherein said fabric has a multiple layer construction including one or more layers of fabric and optionally one or more layers of foam.

6. The body shaping garment of claim 1, wherein said fabric laminate includes one or more layers of fabric, one or more layers of foam, and one or more layers of a polymeric dispersion.

7. The body shaping garment of claim 1, wherein said polymeric dispersion is selected from the group consisting of polyurethaneurea dispersion, polyurethane dispersion, polyolefin dispersion, and combinations thereof.

8. The body shaping garment of claim 1 which is a brassiere with cups further comprising one or more polymeric dispersions in selected portions of the cups and/or adjacent to any underwire.

9. The body shaping garment of claim 1 which is a panty with one or more polymeric dispersions providing tummy control.

\* \* \* \* \*